United States Patent [19]

Salsarulo

[11] 4,303,389
[45] Dec. 1, 1981

[54] INSTRUMENT FOR THE CLINICAL APPLICATION OF FILLINGS FOR DENTAL CAVITIES

[76] Inventor: Angelo Salsarulo, 45, rue Jean Mermoz, F-78620 Etang-la-Ville, France

[21] Appl. No.: 158,911

[22] Filed: Jun. 12, 1980

[30] Foreign Application Priority Data

Jun. 12, 1979 [FR] France .................................. 79 14929

[51] Int. Cl.³ .............................................. A61C 9/00
[52] U.S. Cl. ...................................................... 433/40
[58] Field of Search ............................ 433/39, 40, 139

[56] References Cited

U.S. PATENT DOCUMENTS 2,538,486  1/1951  Tofflemire ............................ 433/39

*Primary Examiner*—Robert Peshock

[57] ABSTRACT

An instrument for the clinical application of fillings for dental cavities comprises a matrix retainer and a proximal central matrix provided with a detachable element for ensuring that the tooth considered is in contact with the adjacent tooth after filling of the cavity. The detachable contact element is provided with an anchoring member and inserted in a cutout formed in the matrix. After setting of the filling material within the dental cavity, the detachable element remains incorporated in the material by means of the anchoring member.

6 Claims, 7 Drawing Figures

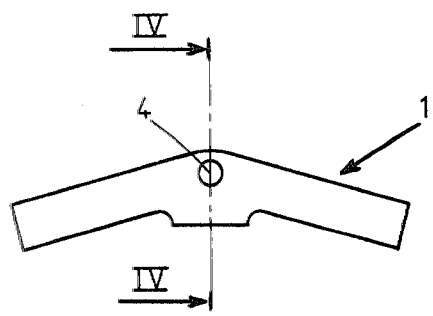
FIG_1
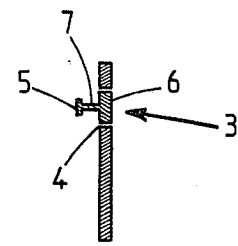
FIG_4
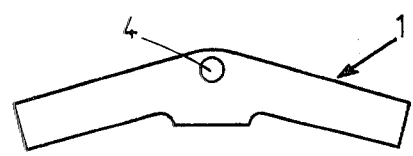
FIG_2
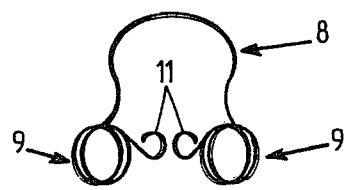
FIG_5
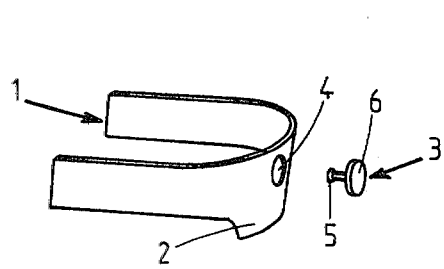
FIG_3
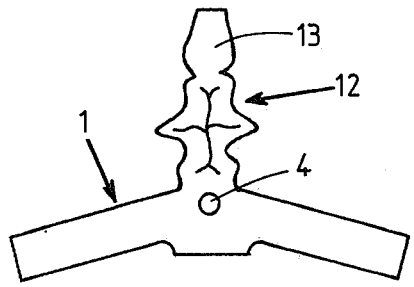
FIG_6
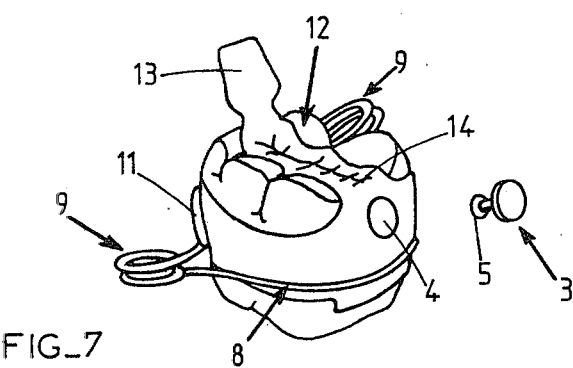
FIG_7

INSTRUMENT FOR THE CLINICAL APPLICATION OF FILLINGS FOR DENTAL CAVITIES

This invention relates to an instrument for the clinical realization of dental cavity fillings. A dental filling operation is performed by means of a plastic-phase material consisting of amalgam or composite resin inserted in a proximal-occlusal dental cavity.

Known instruments of this type which have been in use up to the present time fail to permit a satisfactory proximal contact without preliminary separation of the tooth concerned with respect to the adjacent tooth. Occlusal sculpture of the filling is carried out with hand instruments and the resulting state of surface makes it essential to perform a polishing operation which is both tedious and time-consuming. Furthermore, the usual matrix retainer which serves to hold the matrix in position around the tooth requires the insertion of a wooden wedge in order to prevent cervical overflow of the filling.

The aim of the invention is to overcome the different disadvantages mentioned in the foregoing.

In accordance with the invention, the instrument for filling dental cavities comprises a matrix retainer and aelement for ensuring that the tooth considered is in contact with the adjacent tooth after filling of the cavity. Said detachable element is inserted in a cutout formed in the matrix and adapted to remain incorporated in a dental-cavity filling material after setting of said material, by means of an internal anchoring member embedded in said material.

Thus the matrix device in accordance with the invention together with its detachable proximal contact materialized by the element aforesaid and inserted in the filling permits immediate formation of a surface or point contact which is clinically valid and highly polished. In fact, the surface of the detachable contact element having the design function of establishing an effective contact with the adjacent tooth is prepared beforehand so as to be given a high polish. These two results have never been obtained extemporaneously up to the present time with such materials as amalgam or composite resin.

In accordance with a distinctive feature of the invention, the matrix cutout and the element inserted in this latter have any required shape up to the limit corresponding to the proximal face of the tooth.

In one embodiment of the invention, the matrix comprises an upper portion representing an anatomical face and sculptured so as to reproduce an occlusal sculpture of the tooth in the filling material by means of a compressing or condensing operation.

The pre-formed occlusal face of the matrix permits rapid anatomical sculpture and a state of surface which makes it possible to perform the polishing operation both easily and rapidly.

In an improved embodiment, the invention also makes provision for a matrix retainer consisting of a metallic ring so shaped as to clamp the matrix against the tooth. Said ring is open on one side and provided at each end with a lateral coil located at the level of the proximal face opposite to that of the filling in order to ensure that, by bearing on said proximal face, said ring has the effect of curving the matrix against the cervical edge of the dental cavity under the action of a force applied in a direction opposite to said cavity.

The matrix retainer in accordance with the invention dispenses with the need to insert a wooden wedge by reason of the fact that the matrix is curved against the cervical edge of the dental cavity.

These and other features of the invention will be more apparent upon consideration of the following description and accompanying drawing which illustrates a preferred form of construction of the instrument in accordance with the invention, and in which:

FIG. 1 is a view in elevation of the external face of a first embodiment of the matrix in accordance with the invention, without the upper occlusal element;

FIG. 2 is a view in elevation which is similar to FIG. 1 and shows the internal face of the matrix;

FIG. 3 is a view in perspective showing the simple matrix of FIGS. 1 and 2 together with its detachable contact element;

FIG. 4 is a vertical sectional view along line IV—IV of the matrix of FIG. 1 at the level of its cutout and of its contact element;

FIG. 5 is a top view of a matrix retainer which can be associated with the matrix of FIGS. 1 to 4;

FIG. 6 is an overhead plan view of a second improved embodiment of the matrix in which this latter is provided with an upper occlusal morphological element;

FIG. 7 is a view in perspective of a tooth and of an instrument in accordance with the invention, said instrument being placed on said tooth and provided with the matrix of FIG. 6 and the matrix retainer of FIG. 5.

The matrix 1 shown in FIGS. 1 to 3 is a simple matrix without the upper occlusal morphological element. Said matrix 1 is constituted by a band which can be formed, for example, of stainless steel or of aluminum, or of any other suitable alloy or plastic material having a thickness ranging from 2/100ths to 1/10th of a millimeter, for example. The length and the width of the band vary with the anatomy of the corresponding tooth. This band has a central proximal portion 2 provided with a detachable element 3 for establishing a contact between the tooth considered and the adjacent tooth after filling of the dental cavity (not shown in the drawings). The contact element 3 is inserted in a cutout 4 formed in the central proximal portion 2 and is provided with an internal anchoring member 5 which is embedded in the material employed for filling the dental cavity, said contact element being thus adapted to remain incorporated in the filling material after this latter has been allowed to set.

In the example of construction which is illustrated in FIGS. 3 and 4, the element 3 is similar to a nail provided with a flat head 6 having a highly polished external surface and with a stem 7, the retaining or anchoring member 5 being formed at the end of said stem 7. However, the detachable element 3 can also be a hook, a metal ball or else a chemical retention element of the type involving adhesion with epoxy resins, cyanoacrylates, silicones and so forth.

The cutout 4 is formed at the point of contact with the adjacent tooth, the contact element 3 being intended to remain inserted in the filling material at the time of condensation of this latter within the dental cavity. Thus the polished head 6 on the external face of the matrix 1 materializes the true proximal contact of the filling once the material has been allowed to set and the matrix 1 has been removed.

Said contact head can be of any shape such as round, square, rectangular, oval, trapezoidal, and can have variable dimensions up to the limit corresponding to the proximal face of the tooth, the opening or cutout 4 being given a shape corresponding to said head.

At the time of manipulation by the practitioner, that is, while filling of the dental cavity is in progress, the contact element 3 and the matrix 1 are secured to each other by any suitable means, by applying an adhesive tape on the outer face of the matrix 1 and on the head 6 of the element 3. The adhesive tape may consist of adhesive film, paper or fabric, or may alternatively consist of adhesive wax. It should be understood, however, that any other suitable method may be adopted for attaching and separating the two elements 1 and 3. In the case of an adhesive tape of paper, film or fabric, the tape is provided on the outer face with a small window having dimensions smaller than the element 3 so as to permit the appropriate contact between said element 3 and the adjacent tooth.

In the example considered, and since the element 3 is in fact made integral with the matrix 1, these two parts are preferably formed of the same material but may also be formed of different material if so desired. In this case, the proximal contact is an added part having the same dimensions as the contact element and rigidly fixed to the matrix by means of one of the aforementioned methods of bonding by adhesion. Said added part can be of gold or of different precious or semi-precious alloys, nickel-chromium, steel, dental ceramic or other materials such as synthetic resin materials which are compatible with buccal conditions.

The matrix retainer 8 illustrated in FIG. 5 is a metallic ring so shaped as to clamp the matrix 1 against the tooth. The ring 8 is open on one side and provided at each end with a lateral coil 9 consisting of a double loop 11 located at the level of the proximal face which is opposite to that of the filling. By virtue of this arrangement, the ring is brought to bear on said proximal face (as shown in FIG. 7) and has the effect of curving the matrix 1 against the cervical edge of the dental cavity under the action of a force exerted in a direction opposite to said cavity.

In a second improved embodiment of the invention which is illustrated in FIGS. 6 and 7, the matrix has an upper portion 12 representing an anatomical face and sculptured so as to reproduce an occlusal tooth sculpture in the filling material by means of a compressing or condensing operation. The sculptured portion 12 is adjacent to the band which forms the rest of the matrix and which is identical with the matrix 1 shown in FIGS. 1 to 3. On the side remote from said matrix, said sculptured portion is provided with an extension in the form of a tongue 13 which serves to facilitate manipulation of the instrument.

In the embodiment shown in FIG. 7, the occlusal sculpture of the portion 12 is that of a molar tooth.

Thus the instrument in accordance with the invention and constituting an integral boxing of the tooth with its proximal contact with the adjacent tooth comprises three complementary portions which can nevertheless be employed separately according to the technique adopted by the practitioner, that is, the simple matrix 1, the upper portion 12 of the boxing which is formed in a single piece with the simple matrix 1 and reproduces the occlusal morphology of the tooth concerned, and the matrix retainer consisting of the ring 8. The upper occlusal portion 12 makes it possible after condensation of the filling material within the dental cavity to reproduce an anatomical occlusal sculpture and a state of surface which is ready to be polished. These two portions, namely the simple matrix 1 and the upper occlusal portion 12, are joined together at the level of the marginal ridge 14.

The matrix retainer 8 which serves to maintain the boxing in position is a round-section, square-section or rectangular-section wire which can have a thickness within the range of 0.7 to 1 mm approximately and is formed of stainless steel. Said wire forms an open ring with its two lateral coils 9 placed at the level of the opposite proximal face of the tooth. The two coils which are thus placed in position are supported by this proximal face and exert a mesio-distal force, or conversely, which applies the matrix against the cervical edge of the cavity.

The matrix 1, the contact element 3 and the upper occlusal portion 12 can be made of metal (stainless steel, aluminum or an alloy) or of plastic material (synthetic resin). However, the detachable contact element 3 can be fabricated from a material which is different from the matrix 1 and includes a gold alloy, nickel-chromium, steel, dental ceramic, synthetic resin or any other material which is compatible with buccal conditions.

The invention is not limited to the embodiments described in the foregoing and may accordingly extend to any alternative forms of construction.

What is claimed is:

1. An instrument for the clinical application of fillings for dental cavities, comprising a matrix retainer and a matrix having a cutout that is entirely surrounded by the material of the matrix, a detachable element disposed in said cutout formed in the matrix and being adapted to remain incorporated in filling material for said dental cavity after setting of the filling material by means of an internal anchoring member embedded in said material, and means detachably securing the detachable element to the rest of the matrix while filling of the dental cavity is in progress.

2. An instrument according to claim 1, wherein the detachable element has an external surface that is flush with the adjacent external surface of the matrix.

3. An instrument according to claim 1, wherein the detachable element is secured to the rest of the matrix while filling of the dental cavity is in progress, by applying an adhesive tape or adhesive wax on the outer face of said matrix.

4. An instrument according to claim 1 wherein the detachable element is an adhesive clinical retaining element consisting for example of epoxy resin, cyanoacrylate or silicone.

5. An instrument according to claim 1, wherein the matrix comprises an upper portion representing an anatomical face and sculptured so as to reproduce an occlusal sculpture of the tooth in the filling material by means of a compressing or condensing operation.

6. An instrument according to claim 1, wherein the matrix retainer is a metallic ring shaped in such a manner as to clamp the matrix aganst the tooth, said ring being open on one side and provided at each end with a lateral coil located at the level of the proximal face opposite to that of the filling so as to bear on said proximal face and thus have the effect of curving the matrix against the cervical edge of the dental cavity under the action of a force applied in a direction opposite to said cavity.

* * * * *